United States Patent [19]

Fürther

[11] 4,446,970

[45] May 8, 1984

[54] DIABETIC SET

[76] Inventor: Günter Fürther, Oberfürbergerstrasse 26, 8510 Fürth, Fed. Rep. of Germany, D 8510

[21] Appl. No.: 285,572

[22] Filed: Jul. 21, 1981

[30] Foreign Application Priority Data

Aug. 1, 1980 [DE] Fed. Rep. of Germany ....... 3029226

[51] Int. Cl.³ .............................................. B65D 69/00
[52] U.S. Cl. .................................... 206/569; 206/38; 206/223; 206/570; 206/571; 206/591
[58] Field of Search ............... 206/569, 571, 373, 486, 206/489, 488, 558, 562, 591, 592, 593, 594, 38, 223, 232, 366, 430, 433, 570; 217/52, 53, 35

[56] References Cited

U.S. PATENT DOCUMENTS

| | | | |
|---|---|---|---|
| 191,607 | 6/1877 | Millard | 206/223 |
| 799,593 | 7/1904 | Dohme | 229/15 |
| 1,582,823 | 6/1923 | Jones | 206/591 |
| 1,995,799 | 4/1935 | Doniger | 206/571 |
| 2,093,537 | 9/1937 | Balint | 206/571 |
| 2,410,928 | 11/1946 | Christner et al. | 206/569 |
| 2,426,865 | 9/1947 | Fink | 229/27 |
| 2,740,516 | 4/1956 | Renn | 206/38 R |
| 3,670,938 | 6/1972 | Brocato | 206/562 |
| 3,917,456 | 11/1975 | Eckstein et al. | 206/569 |
| 4,212,390 | 7/1980 | Raczkowski et al. | 206/592 |
| 4,250,998 | 2/1981 | Taylor | 206/571 |
| 4,321,998 | 3/1982 | van de Walker et al. | 206/38 R |
| 4,339,633 | 7/1982 | Cillario | 206/562 |

Primary Examiner—Joseph Man-Fu Moy
Assistant Examiner—David T. Fidei
Attorney, Agent, or Firm—Bacon & Thomas

[57] ABSTRACT

An improved diabetic set in the form of a pressure resistant case for containing at least one insulin bottle, a syringe and, optionally, a supply of alcohol cloths or similar accessories for sterilization. The case includes a container and a lid that preferably telescopically encloses the container in the manner of a cap. The container includes means for releasably securing the insulin bottle and syringe in such a manner as to facilitate hygienic administration of insulin under all conditions.

1 Claim, 11 Drawing Figures

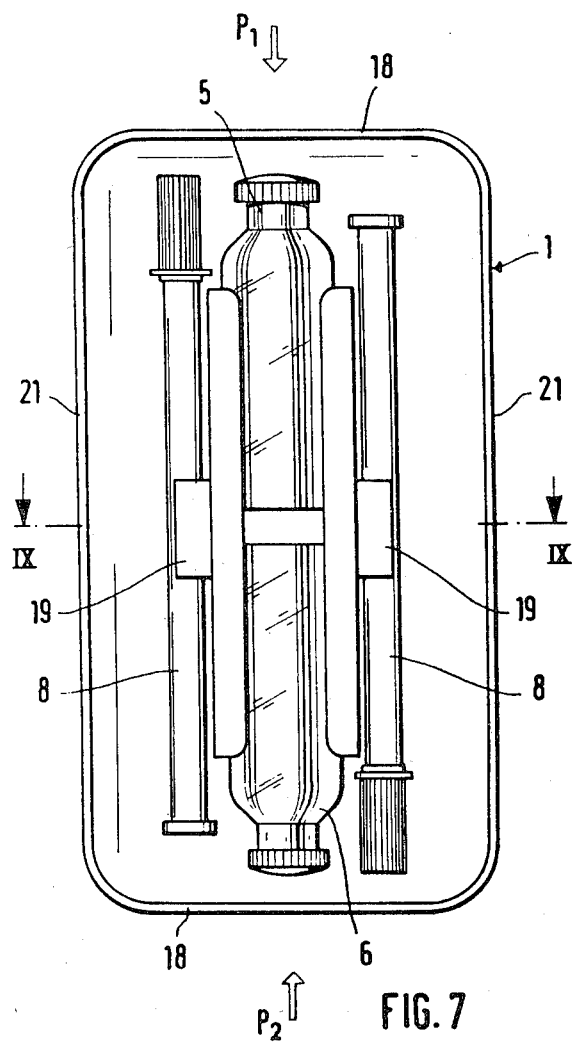
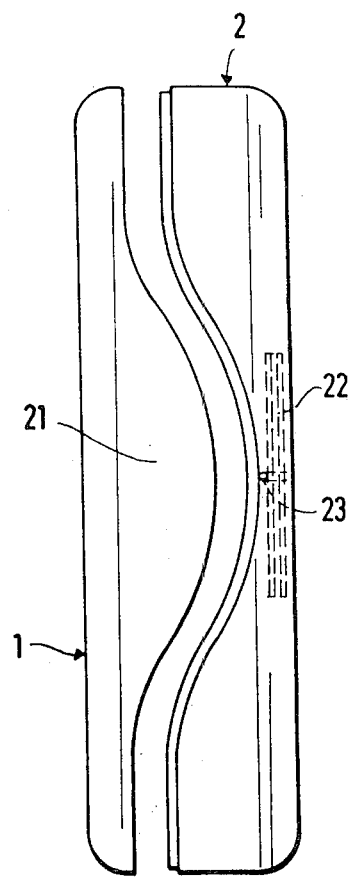
FIG. 7
FIG. 8
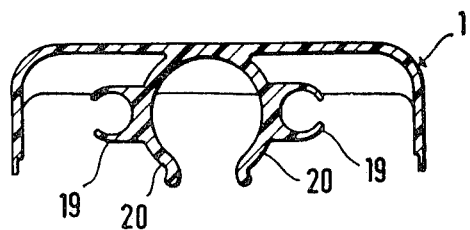
FIG. 9

DIABETIC SET

BACKGROUND OF THE INVENTION

The invention generally relates to the field of technology involving diabetic sets which comprise a pressure resistant housing for containing at least one insulin bottle, a syringe and, optionally, a plurality of alcohol cloths or similar accessories.

The invention specifically relates to an improved diabetic set which provides the advantage of permitting the diabetic patient to carry the set on his person at all times and without excessive space requirements, with the set providing all necessary provisions for administering one or more insulin injections. The invention provides diabetic patients with complete freedom and independence while traveling since necessary insulin injections can be immediately administered by the patient to himself whenever the need arises and wherever the patient might be at the time, such as in a restaurant or other public facility.

Heretofore diabetic sets generally consist of a case provided with a top wall in the form of a hinged lid that is swiveled open to provide access to syringes, insulin bottles and other accessories disposed within the case. In order to administer an injection with such a device, the user must first remove the insulin bottle and the syringe from the case and place same on a support surface. Since the administration of insulin injections outside of the home frequently occurs in public restrooms or similar locations, this procedure is obviously difficult to accommodate since such environments normally lack suitable support surfaces for holding the diabetic set components, but also are characterized by unhygienic conditions. Thus, by their very nature, known diabetic sets are inconvenient and can only be used under limited circumstances.

SUMMARY OF THE INVENTION

It is therefore the object of the present invention to provide an improved diabetic set which may be utilized by the diabetic patient without the need for releasing the case or components contained therein from the hands of the user in order to permit the user to administer an insulin injection under all conditions while observing the highest possible hygienic requirements.

It is another object of the invention to provide an improved diabetic set having a case which is resistant to fracture or breakage and is capable of safely protecting the components contained therein against damage should the diabetic set be dropped.

To attain these and other objects which will become apparent, the invention provides a diabetic set which comprises a case that includes a container and a removable lid which closes the container in a cap-like manner, with the container being designed with holders for releasably securing a syringe and adjacent insulin bottle such that the syringe may be inserted into the insulin bottle after its removal while maintaining the insulin bottle in its holder. The lid may be designed to open on one side of the container to obviate the necessity of removing the insulin bottle from the container for the insertion of the syringe. Such a configuration provides greater rigidity and a higher structural strength against breakage or fracture for the entire diabetic set.

It is preferred that the insulin bottles are secured within the case with the heads of the bottles being exposed in all directions so that possible accidental removal of the lid during application will not result in any interference from a hygienic standpoint. It is also possible to attach the lid to the container by means of a connecting band so that it will simply remain suspended when opened or it may be designed to be inserted from the opposite side in the bottom of the container so that the syringe can be inserted into the insulin bottle from its freely exposed upper end.

In one embodiment of the invention, the holders for the insulin bottles are disposed in such a manner that bottles of different diameters and/or lengths may be accommodated. The range of potential variation in insulin bottle sizes is presently not very broad since commercially available insulin bottles, such as those of major manufacturers, differ in their respective diameters by only a few millimeters. The holders may be designed in the form of laterally slit tubular sections made from an elastic or springy material, such as synthetic plastic. Thus, all conventional insulin bottles may be easily accommodated within a single type of case according to the invention or, in any event, by only a few basic variations thereof.

According to a particularly advantageous embodiment of the invention, the case may be designed in the configuration of the well known slip-in eyeglass case and having an oval-shaped cross section. The container of this case may, at least at its upper end, have a dumbbell-like configuration in its cross section as defined by two lateral sleeves within which the insulin bottles are inserted, with a web connecting the sleeves. Flexible or snap-action holders may be provided in this embodiment for securing the syringes. Since conventional insulin bottles are relatively compact and substantially shorter than syringes, the sleeves for the insertion of the bottles may be made longer to provide room for accommodating a reserve bottle under each insulin bottle. The provision of two lateral slide-in sleeves for the insulin bottles are selectively accessible after removal of the lid and not only serve the purpose of insuring the availability of a larger insulin supply, but provide the advantage of permitting the injection of two different types of insulin at the same time by diabetic patients having this need.

In the aforementioned embodiment wherein the case is in the shape of a conventional eyeglass case, it is particularly advantageous to dispose the web approximately in the center plane of the slide-in sleeves and make the lid relatively long so that only a short oval-shaped sleeve need be provided at the lower end of the container. This permits the web to protrude freely over the greater part of its length following removal of the lid so that it is not necessary to pull out the syringes from narrow channels since only their ends are disposed in the short sleeve, with removal or insertion of the syringes being accomplished by only a simple forward or rearward swiveling action. In order to guard against removal of the protective caps from the syringes, the holders for the syringes are preferably separated from each other by means of a spacer which may, for example, be in the form of a longitudinal rib fastened to the web. The syringes are thus protectively held in a trough formed by the lateral slide-in sleeves for the insulin bottles so that there is no danger of breaking the syringes if the case should be dropped, even with the lid already removed therefrom. The walls of the lower oval-shaped tubular section disposed parallel to the center web not only provides space for containing the ends of the syringes, but also provides opposite side space for alcohol cloths which are used to disinfect the location of the injections on the body of the user.

It is particularly advantageous to design the holders for the insulin bottles so that in their functional position the bottles are partially protruding from the holders to permit viewing their respective labels. This is especially important for diabetic patients who must always use two different types of insulin simultaneously. In this way, they are able to ascertain at a glance the type of insulin contained in the bottle and determine the proportions of the two types required for the injections, with such proportions generally not being equal. In order to still provide a particularly high degree of protection against damage, even in the case of careless handling, a unilateral wall section is provided protruding past the insulin bottles in their holders in the upward direction.

In still another embodiment of the invention, the case may have the configuration of a conventional soap dish with recesses in the lateral wall to provide access to the insulin bottles. The lateral walls may be eliminated altogether, while the longitudinal side walls remain at least in the center area of the container in order to insure better handling during use. This soap dish-like configuration for the case, with the possibility of providing recesses in the two opposing lateral walls, permits the disposition of holders for two insulin bottles facing each other in the longitudinal center line of the container, while clamp holders are disposed for the syringes on both sides laterally adjacent to the holding device for the bottles. The alcohol cloths may be housed within the inside of the lid and secured therein by means of suitable fastening devices, such as a simple rubberband gripping the cloths. Moreover, the lid may be inserted in the lower part of the container after its removal therefrom.

A further embodiment of the invention wherein the configuration of the container is defined by omitted frontal sides to permit accessibility to the insulin bottles from opposing sides without removing the holder also includes a lid that cannot be lost. In this embodiment, the configuration of the case provides a lid in the shape of a rectangular parallelepiped open on one narrow longitudinal side from which the container may be laterally removed, with the container having the configuration of a plate with the omitted wall of the parallelepiped molded thereon. Guides for the slide bearings of the container may be provided, for example, in the form of grooves receiving the open frontal edges of the plate in the frontal walls parallel to the forward direction, of grooves in the top walls parallel to the plate, wherein rudimental ribs of the frontal walls of the container part are guided. It is of particular advantage in this instance to provide extraction stops preventing the complete separation of the lid from the container.

The diabetic set according to the invention may be made from any suitable material and in any suitable manner desired. For example, the case may be integrally molded from synthetic plastic material and provided with a pleasing external appearance, such as a leather-like pattern. It is also understood and within the scope of the invention to use foamed synthetic materials, such as polyurethane foam, which provide a high degree of strength against fracture or breakage while being very low in weight.

These and other objects, advantages, characteristics and details of the invention will become apparent to those skilled in the art by reference to the following description of preferred embodiments thereof when taken in conjunction with the accompanying drawings wherein like reference characters refer to like elements throughout the views.

BRIEF DESCRIPTION OF THE DRAWINGS

FIG. 7 is an elevational view of a diabetic set according to a third embodiment of the invention with the lid removed from the container;

FIG. 8 is a side view of the embodiment of FIG. 7 with the lid shown in a removed condition;

FIG. 9 is a cross-sectional view taken on the line IX—IX in FIG. 7;

DETAILED DESCRIPTION OF THE PREFERRED EMBODIMENTS

Figure 1:
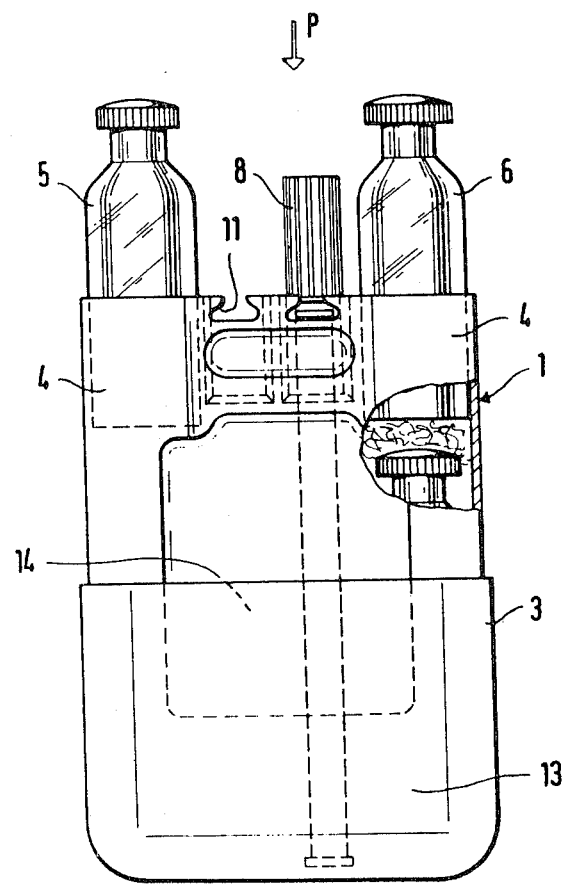
FIG. 1 is an elevational view, partly broken away, of a diabetic set according to a first embodiment of the invention, with the lid removed.
Figure 2:
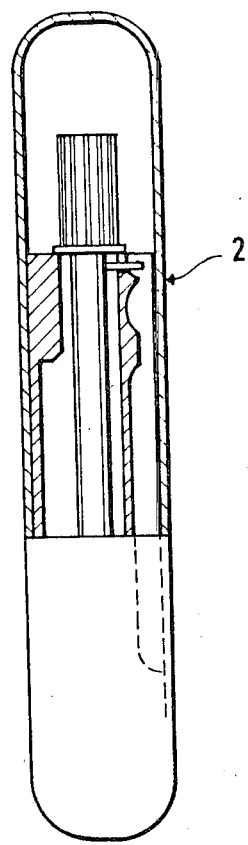
FIG. 2 is a partially sectioned side view of the embodiment of FIG. 1.
Figure 3:
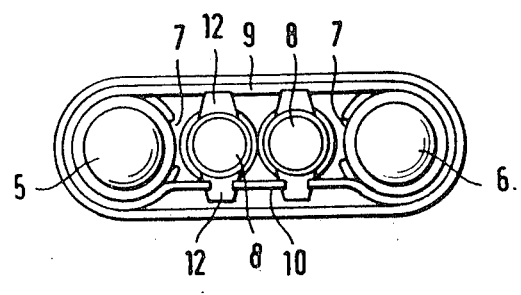
FIG. 3 is a top view of the embodiment of FIG. 1 when viewed in the direction of arrow P in FIG. 1.

A diabetic set according to a first embodiment of the invention is shown in FIGS. 1-3 and consists of a case having the general configuration of a conventional eyeglass case. The case includes a container 1 provided with a removable lid 2 within which container 1 is inserted. Container 1 includes a lower portion 3 having an external surface that is coplanar with the external surface of the lid, thereby providing a smooth external appearance when lid 2 is in its closed position with container 1 inserted therein. Container 1 further includes two lateral insertion sleeves 4 for receiving a pair of insulin bottles 5 and 6. Sleeves 4 are slit, as indicated at 7, so that they are elastically expandable for providing clamping action on insulin bottles 5 and 6 and, further, for accommodating bottles of different diameters. To hold insulin bottles 5 and 6 of relatively short length, sleeves 4 do not necessarily have to extend into lower portion 3, the length of the latter is determined by the length of a pair of syringes 8. As particularly shown in FIG. 3, syringes 8 are releasably secured between sleeves 4 and extend downwardly into lower portion 3. As further shown for this embodiment, sleeves 4 are interconnected by a rear wall 9 and a front wall 10, the latter being recessed with respect to the tangential frontal plane of sleeve 4 thereby defining a space for receiving the syringes therein, with the space being further divided by means of a partition.

A plurality of relief cut grooves 11 are provided in walls 9 and 10 for engaging the opposed transverse lugs 12 on syringes 8, which lugs 12 normally rest against the index and middle fingers of the user during the injection procedure. It is only necessary to provide short guide paths for the syringes between walls 9 and 10, as indicated by the broken line in FIG. 1. This arrangement further insures that the two syringes cannot interfere with each other during their insertion or extraction. Therefore, it is not necessary for sleeves 4 for insulin bottles 5 and 6 to extend over the entire length of container 1. However, if sleeves 4 are extended for the entire length of container 1, this further provides the advantage that additional supply bottles of insulin may be disposed therein in series behind bottles 5 and 6, the latter two bottles protruding in front from container 1.

The offsetting to the rear of frontal wall 10 with respect to the frontal plane 13 of lower portion 3 of container 1, wherein plane 13 coincides with the plane tangential to sleeves 4, creates a space 14 for the insertion of alcohol cloths or similar accessories needed for disinfecting the location of the injection on the body of the user.

As is apparent, the diabetic set according to the invention does not require that container 1 be set down on a support surface or that insulin bottles 5 and 6 be removed therefrom. In use, syringe 8 is removed from its holder and inserted into one or the other of insulin bottles 5 and 6 in the direction indicated by arrow P. After filling, syringe 8 is removed from either bottle 5 or 6 and administered by the patient. After injection, syringe 8 is reinserted in its holder and lid 2 is replaced on container 1. In addition to its small size and easy handling and transportability characteristics, the case configuration design of this first embodiment of the invention also provides a very high degree of rigidity and compressive strength so that the possibility of breaking an insulin bottle or a syringe contained therein is practically eliminated, even if the case should be dropped on the ground. This advantage is quite apparent, particularly when the diabetic patient is traveling and cannot readily replace broken or failed diabetic sets.

Figure 4:
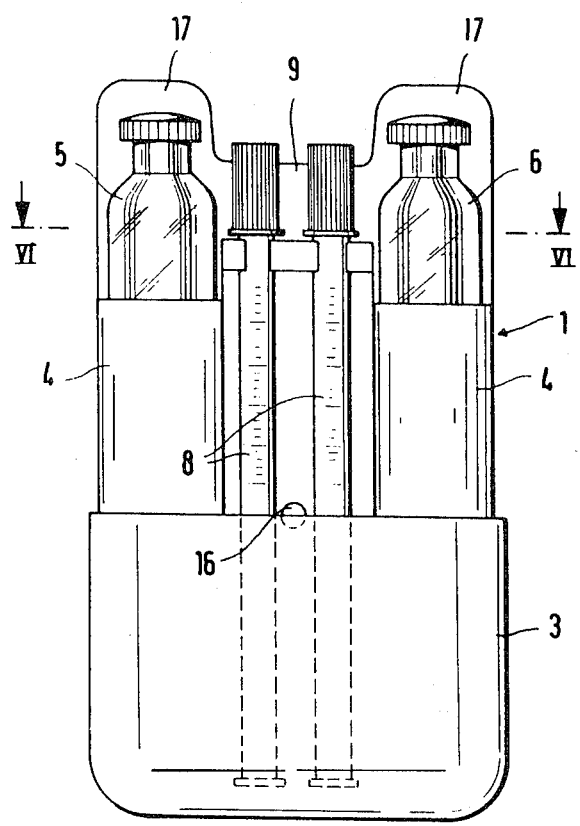
FIG. 4 is an elevational view of a diabetic set according to a second embodiment of the invention.
Figure 5:
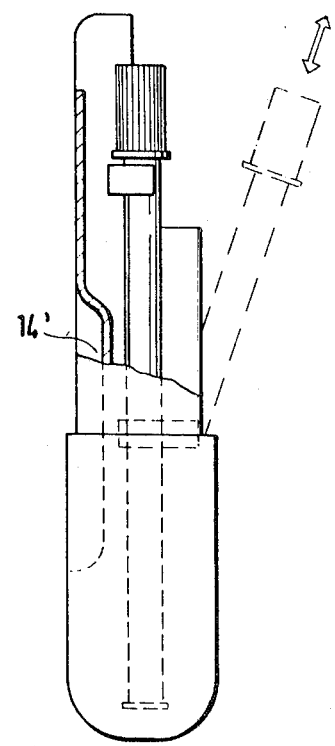
FIG. 5 is a partially broken side view of the embodiment of FIG. 4.
Figure 6:
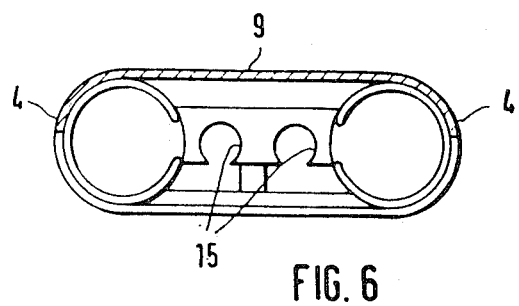
FIG. 6 is a cross-sectional view taken on the line VI—VI in FIG. 4.

A second embodiment of the invention is shown in FIGS. 4-6 wherein the case also has a configuration of a conventional eyeglass case. Front wall 10 in the connecting section between sleeves 4 of the previously described first embodiment is eliminated, with syringes 8 being held directly in front of rear wall 9 in a plurality of locking recesses 15. Syringes 8 are released by rotating same in the forward direction. The physical separation of syringes 8 is accomplished by a bolt 16 projecting forward from rear wall 9 between sleeves 4. Insertion and extraction is effected, as indicated in FIG. 5 by the broken line. Insertion is accomplished by inserting syringe 8 within lower portion 3 and rotating same backwardly into locking engagement with its corresponding recess 15. Extraction of syringe 8 is accomplished by rotating syringe 8 forwardly out of engagement with its recess 15 and removing same from lower portion 3.

Since front wall 10 has been eliminated in this second embodiment, a recessed portion 14' of back wall 9 serves to define a receptacle for receiving and storing alcohol cloths or similar accessories, as shown in FIG. 5. Wall 9 is also provided in the area of insulin bottles 5 and 6 with projections 17 which extend beyond the ends of bottles 5 and 6 to protect them against breakage during handling. As indicated by the design of sleeves 4, insulin bottles 5 and 6 protrude to a considerable extent in front, thereby facilitating the identification of the type of insulin contained within each bottle through its protruding label. This is essential for diabetic patients who must administer two different types of insulin simultaneously.

A third embodiment of a diabetic set according to the invention is shown in FIGS. 7-9. In this embodiment, frontal wall 18 of container 1 is practically eliminated altogether. Accordingly, syringe 8 may receive insulin from either bottle 5 or 6 in the respective directions indicated by arrow P1 from above or arrow P2 from below. Syringes 8 are secured in this embodiment not between insulin bottles 5 and 6 as previously described for the first and second embodiments, but laterally adjacent to bottles 5 and 6. This can be accomplished by molding a pair of clamping holders 19 for syringes 8 directly onto a pair of lateral legs 20 which serve as clamping holders for insulin bottles 5 and 6. A pair of longitudinal side walls 21 of container 1, as particularly shown in FIG. 8, are raised at their midportions in order to permit manual gripping by the user. The lateral walls of lid 2 are shaped in a complementary manner to accommodate the corresponding curved walls of container 1 for engagement with their respective recessed free edges in a manner similar to the usual connection between the dish and lid of a conventional soap holder. To secure alcohol cloths 22 to the case of this embodiment, a holding device 23, such as a rubber strap, is disposed within the interior of lid 2.

Figure 10:
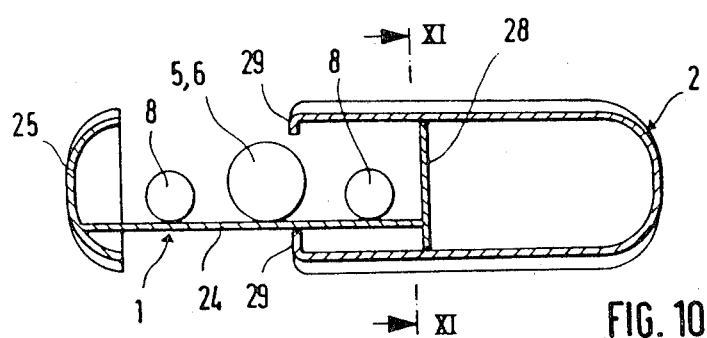
FIG. 10 is a side cross-sectional view of a diabetic set according to a fourth embodiment of the invention.
Figure 11:
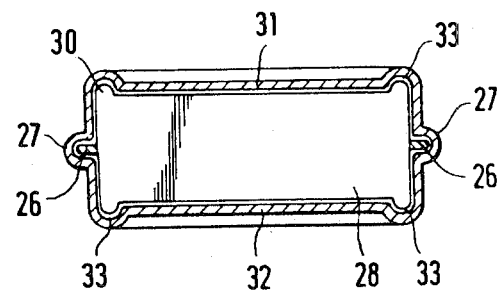
FIG. 11 is a cross-sectional view taken on the line XI—XI in FIG. 10.

A fourth embodiment of the invention is depicted schematically in FIGS. 10 and 11 wherein the case for the diabetic set comprises container 1 which is inserted within and extracted from lid 2 having a cap-like configuration. Container 1 secures insulin bottles 5 and 6, along with syringes 8, on a plate 24 in substantially the same manner as depicted in FIG. 7 for the third embodiment. Insulin bottles 5 and 6 may be pierced by means of syringe 8 from the direction of the frontal sides parallel to the plane of FIG. 10. In the simplest form of this embodiment, container 1 comprises only plate 24 and a longitudinal side wall 25, the latter serving to close off the open front side of cap 2. When container 1 is in its fully inserted position within cap 2, thereby enclosing syringes 8, insulin bottles 5 and 6 and, optionally, a holder for alcohol cloths to be secured on the bottom side of plate 24. Guidance for the insertion and extraction of container 1 with respect to lid 2 is achieved by disposing lateral edges 26 of plate 24 within corresponding grooves defined by projections 27 formed in the side walls of lid 2. An inner longitudinal side wall 28 may also be provided for contact with a pair of border cleats 29 which serve as an extraction stop for container 1. Wall 28 is guided through a plurality of corner extensions 30 which are disposed in correspondingly-shaped channels 33 formed at the corners of lid 2 and extruded from a pair of opposed surfaces 31 and 32. This fourth embodiment of the invention is particularly advantageous because of the coherence of both container 1 and lid 2, even in the extracted operating state. This serves to enhance hygienic handling.

The structural design of the cases, including container, lid and associated parts, for all embodiments of the invention greatly facilitates and simplifies the manufacturing of same, particularly when such cases are made by injection molding or casting synthetic plastic materials, with the container and lid each representing a single integral structural part. This serves to substantially simplify and render economical the production of a diabetic set according to the invention and, moreover, facilitates the imparting of attractive surface designs or patterns on the cases.

The handling of the diabetic set according to the invention without removing the insulin bottles from their container and without the need to set down components of the set is a great advantage and convenience for the diabetic patient. It is to be further understood that the lid in any embodiment may be permanently attached to its associated container by means of a cord or the like so that it may be simply suspended during the administration of an injection, thereby avoiding loss or requiring that the lid be set down prior to use. It is further preferred that the components of the case making up the diabetic set of the present invention have the highest heat insulating properties possible, a characteristic which can be easily obtained by making the cases from foamed plastics or the like. The case should further be both moisture tight and moisture resistant so that it may be stored in a refrigerator for keeping the insulin at a cold temperature.

While several preferred embodiments of the invention have been described herein, many variations thereof will become apparent to those with ordinary skill in the art. Such variations are clearly understood to be within the scope of the present invention as recited in the appended claims.

What is claimed is:

1. In a diabetic set including a housing for containing at least one insulin bottle, at least one injection syringe and, optionally, alcohol cloths or the like, the improvement comprising:
   (a) the housing being pressure resistant and including a container and a removable cap engagable with the container;
   (b) a plurality of slit elastic expandable sleeves carried by the container and extending into the container area over a portion of its length for releasably securing a plurality of insulin bottles therein and permitting free exposure of the entire heads of the bottles;
   (c) a strip disposed between the sleeves;
   (d) a plurality of holders carried by the strip for releasably securing a plurality of syringes through snapfit engagement therewith;
   (e) the container including spaces disposed under the sleeves and coaxial therewith for storing reserve bottles of insulin; and
   (f) the strip is substantially elongate and includes a concave curvature extending for a portion of its length to define space for the optical storage of alcohol cloths.

* * * * *